US011058559B2

(12) United States Patent
Smit et al.

(10) Patent No.: US 11,058,559 B2
(45) Date of Patent: Jul. 13, 2021

(54) ENERGY STORING PROSTHETIC KNEE ACTUATOR

(71) Applicant: Technische Universiteit Delft, Delft (NL)

(72) Inventors: Gerhardus Smit, Delft (NL); Heike Vallery, Delft (NL)

(73) Assignee: TECHNISCHE UNIVERSITEIT DELFT, Delft (NL)

( * ) Notice: Subject to any disclaimer, the term of this patent is extended or adjusted under 35 U.S.C. 154(b) by 0 days.

(21) Appl. No.: 15/789,803

(22) Filed: Oct. 20, 2017

(65) Prior Publication Data

US 2018/0036150 A1    Feb. 8, 2018

Related U.S. Application Data

(63) Continuation of application No. PCT/NL2016/050273, filed on Apr. 19, 2016.

(30) Foreign Application Priority Data

Apr. 20, 2015   (NL) ...................................... 2014674

(51) Int. Cl.
*A61F 2/64* (2006.01)
*A61F 2/74* (2006.01)
(Continued)

(52) U.S. Cl.
CPC .................. *A61F 2/70* (2013.01); *A61F 2/64* (2013.01); *A61F 2002/5003* (2013.01);
(Continued)

(58) Field of Classification Search
CPC ........ A61F 2002/5033; A61F 2002/748; A61F 2002/744; A61F 2002/745; A61F 2002/747
See application file for complete search history.

(56) References Cited

U.S. PATENT DOCUMENTS 6,517,585 B1 * 2/2003 Zahedi ...................... A61F 2/68
                                                    623/24
8,317,874 B2    11/2012 Pusch et al.
(Continued)

FOREIGN PATENT DOCUMENTS

EP        1415626        5/2004
WO        2016/171548    10/2016

*Primary Examiner* — David H Willse
(74) *Attorney, Agent, or Firm* — Peacock Law P.C.; Janeen Vilven; Justin Muehlmeyer

(57) ABSTRACT

An energy storing prosthetic knee actuator and method of using such an energy storing prosthetic knee actuator comprising a hydraulic or pneumatic cylinder with a piston and a piston rod, wherein the piston and the hydraulic or pneumatic cylinder are movable with respect to each other, an energy storage accumulator and a control valve provided in piping connecting the hydraulic or pneumatic cylinder with the energy storage accumulator for controlling an exchange of fluid or gas between the accumulator and the cylinder, wherein the cylinder and the piston are connected to a user's upper leg and lower leg respectively or vice versa, and wherein the actuator is arranged to close the control valve when the user is sitting down and to open the control valve when the user is going to stand or is standing up.

8 Claims, 2 Drawing Sheets

(51) Int. Cl.
*A61F 2/70* (2006.01)
*A61F 2/76* (2006.01)
*A61F 2/50* (2006.01)

(52) U.S. Cl.
CPC ... *A61F 2002/745* (2013.01); *A61F 2002/747* (2013.01); *A61F 2002/748* (2013.01); *A61F 2002/764* (2013.01); *A61F 2002/7615* (2013.01); *A61F 2002/7635* (2013.01)

(56) References Cited

U.S. PATENT DOCUMENTS

| | | |
|---|---|---|
| 2013/0013085 A1 | 1/2013 | Smith et al. |
| 2015/0182354 A1* | 7/2015 | Bonnet ............... A61F 2/64 623/26 |
| 2018/0036148 A1* | 2/2018 | Lincoln ............ A61B 5/4851 |

* cited by examiner

ENERGY STORING PROSTHETIC KNEE ACTUATOR

CROSS-REFERENCE TO RELATED APPLICATIONS

This application is a continuation application of Patent Cooperation Treaty Application No. PCT/NL2016/050273, filed on Apr. 19, 2016, which claims priority to Netherlands Patent Application No. 2014674, filed on Apr. 20, 2015, and the specifications and claims thereof are incorporated herein by reference.

STATEMENT REGARDING FEDERALLY SPONSORED RESEARCH OR DEVELOPMENT

Not Applicable.

THE NAMES OF PARTIES TO A JOINT RESEARCH AGREEMENT

Not Applicable.

INCORPORATION BY REFERENCE OF MATERIAL SUBMITTED ON A COMPACT DISC

Not Applicable.

STATEMENT REGARDING PRIOR DISCLOSURES BY THE INVENTOR OR A JOINT INVENTOR

Not Applicable.

COPYRIGHTED MATERIAL

Not Applicable.

BACKGROUND OF THE INVENTION

Field of the Invention (Technical Field)

The present invention relates to an energy storing prosthetic knee actuator comprising a hydraulic or pneumatic cylinder with a piston and a piston rod, wherein the piston and the hydraulic or pneumatic cylinder are movable with respect to each other and are connected or connectable to a user's upper leg and lower leg respectively or vice versa, and further comprising an energy storage accumulator and at least one control valve provided in piping connecting the hydraulic or pneumatic cylinder with the energy storage accumulator for controlling an exchange of fluid or gas between the energy storage accumulator and the hydraulic or pneumatic cylinder.

Description of Related Art Including Information Disclosed Under 37 C.F.R. §§ 1.97 and 1.98

An energy storing prosthetic knee actuator is known from EP 1 415 626.

US2013/0013085 also teaches an energy storing prosthetic knee actuator, and is provided with at least two controllable variable fluid flow resisting devices and a control system. The control system is actuable to cause storage of the fluid energy for a predetermined length of time and release of the fluid energy at a predetermined time during the gait cycle. Both the storage and the release of the fluid energy are variable by action of the control system.

BRIEF SUMMARY OF THE INVENTION

The invention has as its prime object and aim to provide a mere standing up assist to amputees who have lost at least one of their lower legs including the knee joint. Such an assist is particularly useful for the elderly or other persons having limited physical condition and who would benefit from a device assisting them in standing up from a seated position.

Another object and aim is to provide such a standing up assist which is low weight, and which is capable to regenerate energy that is stored during sitting down and use it for standing up.

Further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention. In the drawings.

DETAILED DESCRIPTION OF THE INVENTION

Figure 1:
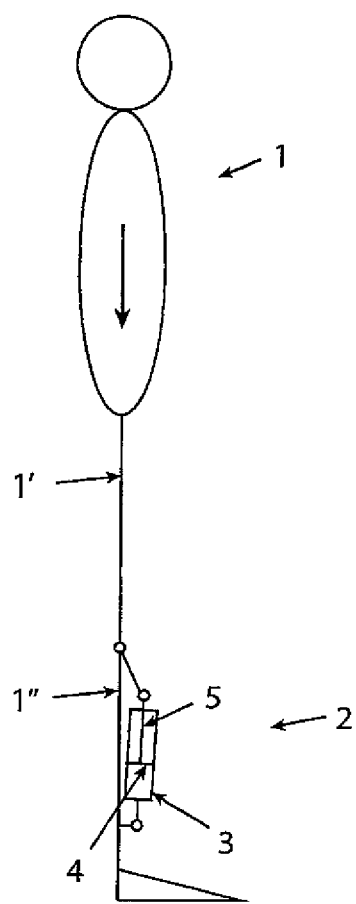
FIG. 1 shows a user standing up and wearing an energy storing prosthetic knee actuator according to the invention.

Surprisingly, the inventors have found that the aims and objects of the invention can at low cost be attained in an energy storing prosthetic knee actuator comprising a hydraulic or pneumatic cylinder with a piston and a piston rod, wherein the piston and the hydraulic or pneumatic cylinder are movable with respect to each other and wherein the actuator comprises an energy storage accumulator and a control valve provided in piping connecting the hydraulic or pneumatic cylinder with the energy storage accumulator, wherein the control valve is automatically operable and connected to at least one sensor for detecting whether the user is standing up. The control valve is then suitably arranged to close off the piping and stop the flow between the hydraulic or pneumatic cylinder and the energy storage accumulator when the at least one sensor detects that the user is seated and to open said piping and thus enable the flow of gas or fluid when the at least one sensor detects that the user is standing up. The control valve is preferably a single control valve. Preferably the cylinder is a pneumatic cylinder.

Using the energy storing prosthetic knee actuator of the invention after connecting the hydraulic or pneumatic cylinder and the piston to a user's upper leg and lower leg respectively or vice versa, enables assisting the standing up of the user by controlling an exchange of fluid or gas between the energy storage accumulator and the hydraulic or pneumatic cylinder, by executing the steps of:

providing at least one sensor for detecting whether the user is seated or standing up;

closing the control valve when the sensor detects that the user is sitting down to maintain the stored energy in the energy storage accumulator that corresponds to the flow of fluid or gas received into the accumulator as induced by the piston moving in the hydraulic or pneumatic cylinder by reason of the user's motion from standing up to sitting; and opening the control valve when the sensor detects that the user intends to stand or is standing up for release of the stored energy from the energy storage accumulator for driving the piston and moving it with respect to the hydraulic or pneumatic cylinder to straighten the user's leg again.

It is possible to use different types of sensors, such as a mechanic, electric or a pneumatic sensor. Preferably the sensor is a load sensor, an accelerometer, an inertial measurement unit, or any suitable combination of any such sensors. Advantageously the sensor or sensors can be combined with a suitable signal processing unit.

One other preferable feature is that the piston is movable along and up to an extremity of the piston rod. In this way, the piston does not hinder extension of the knee when the user is sitting.

It may further be preferable that in addition to the control valve the piping comprises a controllable flow restriction member, which can be used to restrict the speed of the extension of the knee.

It may also be preferable that redundant piping is provided between the hydraulic or pneumatic cylinder and the energy storage accumulator, in which redundant piping a one-way valve is included enabling a flow of fluid or gas from the hydraulic or pneumatic cylinder to the energy storage accumulator. This enables that the user can sit down also when the control valve closes off the piping between the hydraulic or pneumatic cylinder and the energy storage accumulator.

One other preferable feature is that a high-pressure reservoir is provided to connect to the energy storage accumulator. This can compensate for energy losses and leakage and—if desired—can also assist the user when the user has to deliver power such as when walking the stairs.

The invention will hereinafter be further elucidated with reference to the drawing of an exemplary embodiment of an apparatus according to the invention that is not limiting as to the appended claims.

Whenever in the figures the same reference numerals are applied, these numerals refer to the same parts.

Figure 2:
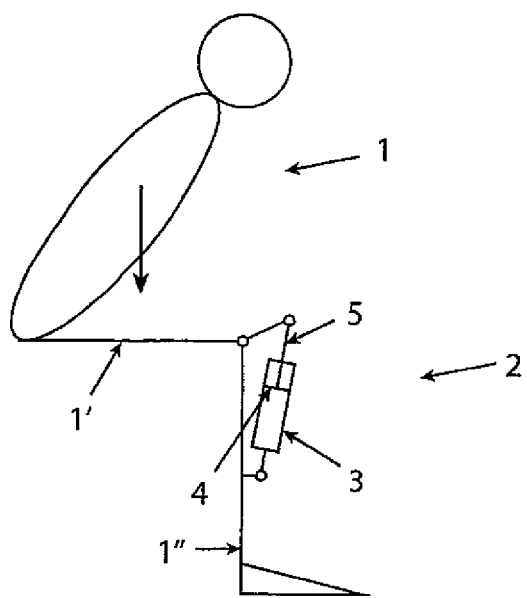
FIG. 2 shows the user of FIG. 1 sitting down.

Making reference first to FIG. 1 and FIG. 2, a user 1 is shown respectively standing up and sitting down, and wearing an energy storing prosthetic knee actuator 2 according to the invention, comprising a hydraulic or pneumatic cylinder 3 with a piston 4 and a piston rod 5. The piston 4 and the hydraulic or pneumatic cylinder 3 are movable with respect to each other and are connected to an upper leg 1' and lower leg 1" of the user 1. The connection can of course also be reversed. Preferably a pneumatic cylinder is applied because of its lower weight than a hydraulic cylinder.

Figure 3:
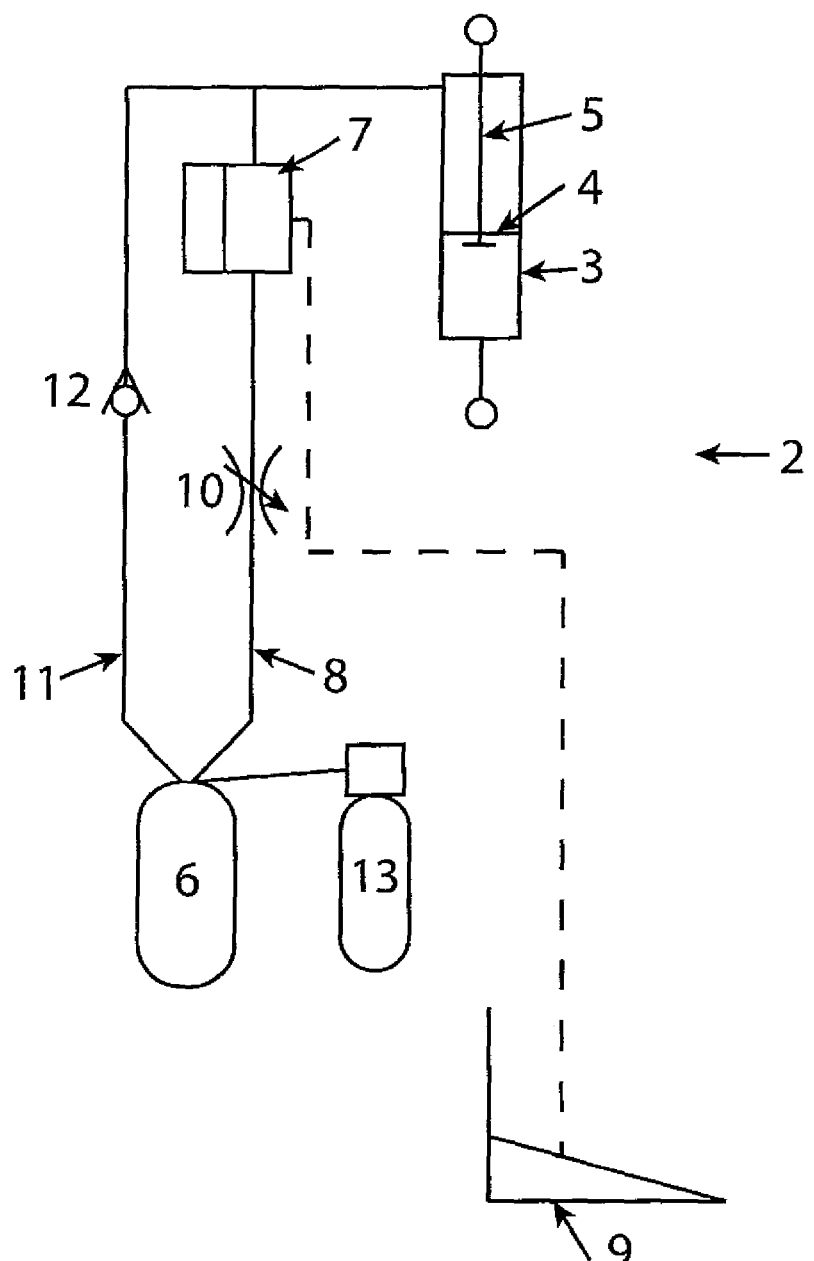
FIG. 3 schematically shows the energy storing prosthetic knee actuator according to the invention.

Making now reference to FIG. 3, it is shown that the actuator 2 further comprises an energy storage accumulator 6 and a control valve 7 provided in piping 8 connecting the hydraulic or pneumatic cylinder 3 with the energy storage accumulator 6. Preferably there is only a single control valve. The energy storing prosthetic knee actuator 2 of the invention thus enables assisting the standing up of the user 1 by controlling an exchange of fluid or gas between the energy storage accumulator 6 and the hydraulic or pneumatic cylinder 3, by executing the steps of:

providing at least one sensor 9 for detection whether the user 1 is seated or standing up;

closing the control valve 7 when the sensor 9 detects that the user is sitting down to maintain the stored energy in the energy storage accumulator 6 that corresponds to the flow of fluid or gas received in the accumulator 6 as induced by the piston 4 moving in the hydraulic or pneumatic cylinder 3 by reason of the user's motion from standing up (FIG. 1) to sitting down (FIG. 2); and opening the control valve 7 when the sensor 9 detects that the user 1 intends to stand up or is standing up for release of the stored energy from the energy storage accumulator 6 for driving the piston 4 and move it with respect to the hydraulic or pneumatic cylinder 3 to straighten the user's leg so that the user 1 eventually can assume again the position shown in FIG. 1.

Although it is possible to include a manual operation, the control valve 7 operates automatically and is therefore connected to the at least one sensor 9, which is for instance provided at the bottom of the lower leg 1", for detecting whether the user 1 is in the process of standing up. According to what is mentioned above the preferably single control valve 7 is then suitably arranged to close off the piping 8 between the hydraulic or pneumatic cylinder 3 and the energy storage accumulator 6 when the sensor 9 detects that the user 1 is seated (as shown in FIG. 2) and to open said piping 8 and enable again the flow of gas or fluid when the at least one sensor 9 detects that the user 1 is in the process of standing up. It is possible to use different types of sensors, such as a mechanic, electric or a pneumatic sensor. Preferably the sensor 9 is selected from the group comprising a load sensor, an accelerometer, an inertial measurement unit, or any suitable combination of any such sensors.

One other preferable feature is that the piston 4 is movable along and up to an extremity of the piston rod 5. In this way, the piston 4 does not hinder extension of the knee when the user 1 is sitting.

In addition to the application of a preferably single control valve 7 the piping 8 comprises advantageously a controllable flow restriction member 10 which can be used to restrict the speed of the extension of the knee.

It may also be preferable that redundant piping 11 is provided between the hydraulic or pneumatic cylinder 3 and the energy storage accumulator 6, in which redundant piping 11 a one-way valve 12 is included enabling a flow of fluid or gas from the hydraulic or pneumatic cylinder 3 to the energy storage accumulator 6. This enables that the user 1 can sit down also when the control valve 7 closes off the piping 8 between the hydraulic or pneumatic cylinder 3 and the energy storage accumulator 6 which would otherwise prevent that the piston 4 moves in the hydraulic or pneumatic cylinder 3 and correspondingly that the knee of the user 1 would be bent.

Finally, a high-pressure reservoir 13 can be provided to connect to the energy storage accumulator 6. This can compensate for possible energy losses and leakage. If desired it can also be used to extend the leg in situations that additional power is required that would otherwise have to be delivered by the user, such as when walking the stairs.

Although the invention has been discussed in the foregoing with reference to an exemplary embodiment of the energy storing prosthetic knee actuator of the invention, the invention is not restricted to this particular embodiment which can be varied in many ways without departing from the principles of the invention. The discussed exemplary embodiment shall therefore not be used to construe the appended claims strictly in accordance therewith. On the contrary the embodiment is merely intended to explain the wording of the appended claims without intent to limit the claims to this exemplary embodiment. The scope of protection of the invention shall therefore be construed in accordance with the appended claims only, wherein a possible ambiguity in the wording of the claims shall be resolved using this exemplary embodiment.

What is claimed is:

1. A single control valve energy storing prosthetic knee actuator comprising:
   - a single sensor-controlled control valve automatically operable and connected to at least one sensor, wherein the at least one sensor is configured to detect whether a user is seated or standing up, and wherein the single sensor-controlled control valve is the only sensor-controlled valve in the actuator;
   - a hydraulic or pneumatic cylinder comprising a piston and a piston rod, wherein the piston and the hydraulic or pneumatic cylinder are movable with respect to each other and are configured to be connected or connectable to the user's upper leg and lower leg respectively or vice versa; and
   - an energy storage accumulator;
   - wherein the sensor-controlled single control valve is disposed in piping connecting the hydraulic or pneumatic cylinder with the energy storage accumulator for controlling an exchange of fluid or gas between the energy storage accumulator and the hydraulic or pneumatic cylinder;
   - and wherein the single sensor-controlled control valve is arranged to close off the piping and stop the flow between the hydraulic or pneumatic cylinder and the energy storage accumulator when the at least one sensor detects that the user is seated, and to open the valve in the piping and thus enable the flow of gas or fluid when the at least one sensor detects that the user is standing up for release of the stored energy from the energy storage accumulator for driving the piston and move it with respect to the hydraulic or pneumatic cylinder to straighten the user's leg again.

2. The energy storing prosthetic knee actuator according to claim 1, wherein the cylinder is a pneumatic cylinder.

3. The energy storing prosthetic knee actuator according to claim 1, wherein the at least one sensor is selected from the group consisting of a load sensor, an accelerometer, an inertial measurement unit, and any suitable combination of any such sensors.

4. The energy storing prosthetic knee actuator according to claim 1, wherein the piston is movable along and up to an extremity of the piston rod.

5. The energy storing prosthetic knee actuator according to claim 1, further comprising a controllable flow restriction member disposed in the piping.

6. The energy storing prosthetic knee actuator according to claim 1, additionally comprising redundant piping between the hydraulic or pneumatic cylinder and the energy storage accumulator, in which redundant piping a one-way valve is included enabling a flow of fluid or gas from the hydraulic or pneumatic cylinder to the energy storage accumulator.

7. The energy storing prosthetic knee actuator according to claim 1, additionally comprising a high-pressure reservoir connected to the energy storage accumulator.

8. A method of using a single control valve energy storing prosthetic knee actuator comprising the steps of:
   - providing a single control valve energy storing prosthetic knee actuator comprising a single sensor-controlled control valve automatically operable and connected to at least one sensor, wherein the at least one sensor is configured to detect whether the user is seated or standing up, and wherein the single sensor-controlled control valve is the only sensor-controlled valve in the actuator, the single sensor-controlled control valve disposed in piping connecting a hydraulic or pneumatic cylinder with an energy storage accumulator for controlling an exchange of fluid or gas between the energy storage accumulator and the hydraulic or pneumatic cylinder, the hydraulic or pneumatic cylinder comprising a piston and a piston rod, wherein the piston and the hydraulic or pneumatic cylinder are movable with respect to each other;
   - connecting the hydraulic or pneumatic cylinder and the piston to a user's upper leg and lower leg respectively or vice versa;
   - closing the single sensor-controlled control valve when the at least one sensor detects that the user is sitting down; and
   - opening the single sensor-controlled control valve when the at least one sensor detects that the user is standing up.

* * * * *